US010350010B2

(12) United States Patent
Kao et al.

(10) Patent No.: US 10,350,010 B2
(45) Date of Patent: Jul. 16, 2019

(54) METHOD AND SYSTEM FOR VERIFYING PANORAMIC IMAGES OF IMPLANTS

(71) Applicant: INTAI TECHNOLOGY CORP., Taichung (TW)

(72) Inventors: Kuo-Tung Kao, Taichung (TW); Chen-Tai Lin, Taichung (TW); Ying-Yi Cheng, Taichung (TW); Shih-Chang Chuang, Taichung (TW); Chih-Yen Chiang, Taichung (TW)

(73) Assignee: INTAI TECHNOLOGY CORP., Taichung (TW)

( * ) Notice: Subject to any disclaimer, the term of this patent is extended or adjusted under 35 U.S.C. 154(b) by 67 days.

(21) Appl. No.: 15/663,817

(22) Filed: Jul. 30, 2017

(65) Prior Publication Data

US 2018/0132940 A1    May 17, 2018

Related U.S. Application Data

(60) Provisional application No. 62/421,995, filed on Nov. 14, 2016.

(30) Foreign Application Priority Data

Apr. 26, 2017   (CN) .......................... 2017 1 0281546

(51) Int. Cl.
*G06K 9/00* (2006.01)
*A61B 34/10* (2016.01)
(Continued)

(52) U.S. Cl.
CPC .......... *A61B 34/10* (2016.02); *A61B 17/7001* (2013.01); *A61B 90/37* (2016.02);
(Continued)

(58) Field of Classification Search
None
See application file for complete search history.

(56) References Cited

U.S. PATENT DOCUMENTS 7,763,035 B2 * 7/2010 Melkent ............. A61B 17/1757
600/424
8,214,014 B2    7/2012 Pacheco
(Continued)

FOREIGN PATENT DOCUMENTS

CN    102933163 A    2/2013
TW      558689 B    10/2003

*Primary Examiner* — Shervin K Nakhjavan
(74) *Attorney, Agent, or Firm* — CKC & Partners Co., LLC

(57) ABSTRACT

A pre-planning interface displaying step of a method for verifying panoramic images of implants is for displaying a picture, a menu and a cursor on a screen. An implant trajectory pattern adding step is for moving the cursor to select an implant adding item by a user and then generating the implant trajectory pattern in the picture. An implant trajectory pattern adjusting step is for controlling the cursor to adjust a position of the implant trajectory pattern and then move the implant trajectory pattern from a starting position to a target position in the picture. A panoramic image verifying step is for rotating the surgical site pattern around the implant trajectory pattern at a viewing angle according to the target position and the implant trajectory pattern as a central axis, and the viewing angle is greater than 0 degrees and smaller than or equal to 180 degrees.

20 Claims, 10 Drawing Sheets

(51) Int. Cl.
   *A61B 17/70* (2006.01)
   *A61B 90/00* (2016.01)
   *G06F 3/0482* (2013.01)
   *G06F 3/0484* (2013.01)
   *G06T 3/60* (2006.01)
   *G06T 3/40* (2006.01)
   *G06F 3/0481* (2013.01)
   *A61B 17/56* (2006.01)

(52) U.S. Cl.
   CPC ........ *G06F 3/0482* (2013.01); *G06F 3/04845* (2013.01); *G06T 3/4038* (2013.01); *G06T 3/60* (2013.01); *A61B 2017/568* (2013.01); *A61B 2034/107* (2016.02); *A61B 2090/364* (2016.02); *A61B 2560/0487* (2013.01); *G06F 3/04815* (2013.01); *G06T 2200/24* (2013.01); *G06T 2210/41* (2013.01)

(56) References Cited

U.S. PATENT DOCUMENTS

| | | | | |
|---|---|---|---|---|
| 8,228,560 | B2* | 7/2012 | Hooper | G06T 5/20 348/606 |
| 8,891,847 | B2* | 11/2014 | Helm | G06T 11/00 382/131 |
| 2003/0026469 | A1* | 2/2003 | Kreang-Arekul | G06K 9/32 382/132 |
| 2003/0055503 | A1* | 3/2003 | O'Neil | A61F 2/442 623/17.11 |
| 2004/0044295 | A1* | 3/2004 | Reinert | A61B 34/20 600/587 |
| 2005/0192575 | A1* | 9/2005 | Pacheco | A61B 17/1671 606/86 A |
| 2007/0073290 | A1* | 3/2007 | Boehm, Jr. | A61B 17/1703 606/328 |
| 2010/0296716 | A1* | 11/2010 | Hanssen | G06T 7/0012 382/131 |
| 2011/0093051 | A1* | 4/2011 | Davis | A61N 1/372 607/116 |
| 2013/0066647 | A1* | 3/2013 | Andrie | G06Q 10/06311 705/2 |
| 2014/0081659 | A1* | 3/2014 | Nawana | G16H 50/20 705/3 |
| 2014/0357985 | A1* | 12/2014 | Cardelino | A61B 6/12 600/424 |
| 2016/0117817 | A1* | 4/2016 | Seel | G06T 7/0014 382/131 |
| 2017/0119472 | A1* | 5/2017 | Herrmann | A61B 34/10 |
| 2017/0231702 | A1* | 8/2017 | Crawford | A61B 17/025 700/254 |
| 2018/0262743 | A1* | 9/2018 | Casas | H04N 13/296 |

* cited by examiner

METHOD AND SYSTEM FOR VERIFYING PANORAMIC IMAGES OF IMPLANTS

RELATED APPLICATIONS

This application claims priority to U.S. Provisional Application Ser. No. 62/421,995 filed Nov. 14, 2016, and China application No. 201710281546.2 filed on Apr. 26, 2017, the disclosures of which are incorporated herein by reference in their entireties.

BACKGROUND

Technical Field

The present disclosure relates to a method and a system for verifying images of implants. More particularly, the present disclosure relates to a method and a system for verifying panoramic images of implants.

Description of Related Art

In general medical institutions, a preoperative planning for surgery has already become a basic topic. Many surgical operations require high accuracy and rich experience. If there is a slight error in the surgical operation, it may cause huge damage at a surgical site.

In a conventional surgical process, placement of bone screws into the human spine is a common surgical procedure to allow for a multitude of spinal surgeries to be performed. The bone screws are typically placed into a vertebral body. However, adjacent to the spine are numerous vital structures and organs, in particular the cervical and thoracic spine regions, which have very low tolerance for surgically created injuries that may ultimately lead to significant morbidity and/or mortality. For this reason, the majority of research focus on placement of the bone screws is centered on improving accuracy to maintain the bone screw within a bony (the vertebral body) environment. Therefore, a method and a system for verifying panoramic images of implants having the features of high accuracy, high precision and convenient operation are commercially desirable.

SUMMARY

According to one aspect of the present disclosure, a method for verifying panoramic images of implants and checking a relative position between an implant trajectory pattern and a surgical site pattern provides a pre-planning interface displaying step, an implant trajectory pattern adding step, an implant trajectory pattern adjusting step and a panoramic image verifying step. The pre-planning interface displaying step is for displaying at least one picture, a menu and a cursor on a screen, and the picture has the surgical site pattern. The implant trajectory pattern adding step is for moving the cursor to select an implant adding item of the menu by a user and then generating the implant trajectory pattern in the picture, and the implant trajectory pattern is located at a starting position. The implant trajectory pattern adjusting step is for controlling the cursor to adjust a position of the implant trajectory pattern and then move the implant trajectory pattern from the starting position to a target position in the picture. The panoramic image verifying step is for rotating the surgical site pattern around the implant trajectory pattern at a viewing angle according to the target position and the implant trajectory pattern as a central axis, and the viewing angle is greater than 0 degrees and smaller than or equal to 180 degrees.

According to another aspect of the present disclosure, a system for verifying panoramic images of implants and checking a relative position between an implant trajectory pattern and a surgical site pattern includes a screen and a processing unit. The screen displays at least one picture, a menu and a cursor, and the picture has the surgical site pattern. The processing unit is signally connected to the screen. The processing unit includes an implant trajectory pattern adding module, an implant trajectory pattern adjusting module and a panoramic image verifying module. The implant trajectory pattern adding module is configured to move the cursor to select an implant adding item of the menu by a user and then generate the implant trajectory pattern in the picture. The implant trajectory pattern is located at a starting position. The implant trajectory pattern adjusting module is signally connected to the implant trajectory pattern adding module. The implant trajectory pattern adjusting module is configured to control the cursor to adjust a position of the implant trajectory pattern and then move the implant trajectory pattern from the starting position to a target position in the picture. The panoramic image verifying module is signally connected to the implant trajectory pattern adjusting module. The panoramic image verifying module is configured to rotate the surgical site pattern around the implant trajectory pattern at a viewing angle according to the target position and the implant trajectory pattern as a central axis, and the viewing angle is greater than 0 degrees and smaller than or equal to 180 degrees.

BRIEF DESCRIPTION OF THE DRAWINGS

The present disclosure can be more fully understood by reading the following detailed description of the embodiment, with reference made to the accompanying drawings as follows.

DETAILED DESCRIPTION

Figure 1A:
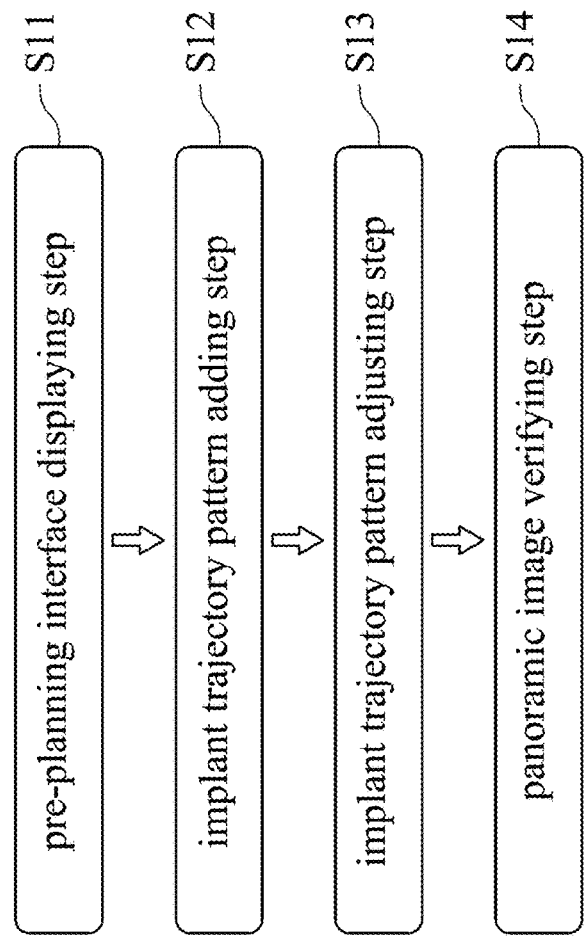
FIG. 1A shows a flow chart of a method for verifying panoramic images of implants according to one embodiment of the present disclosure.
Figure 1B:
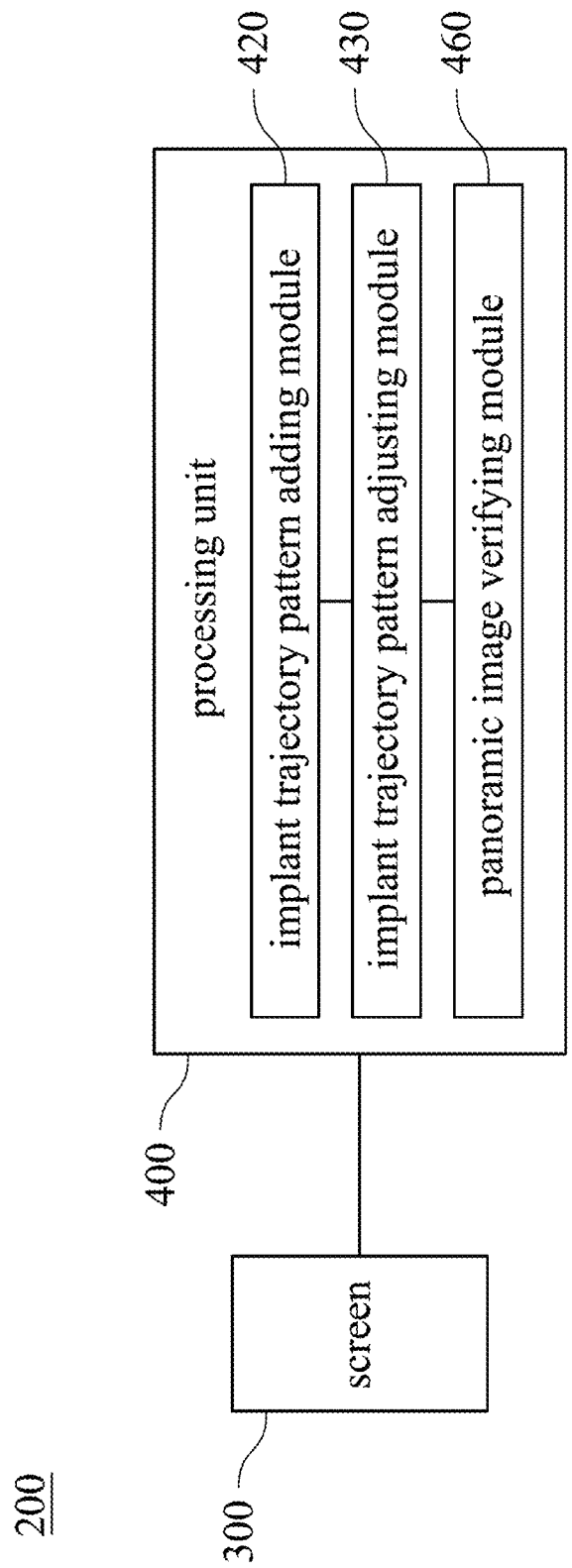
FIG. 1B shows a block diagram of a system for verifying panoramic images of implants according to one embodiment of the present disclosure.
Figure 3:
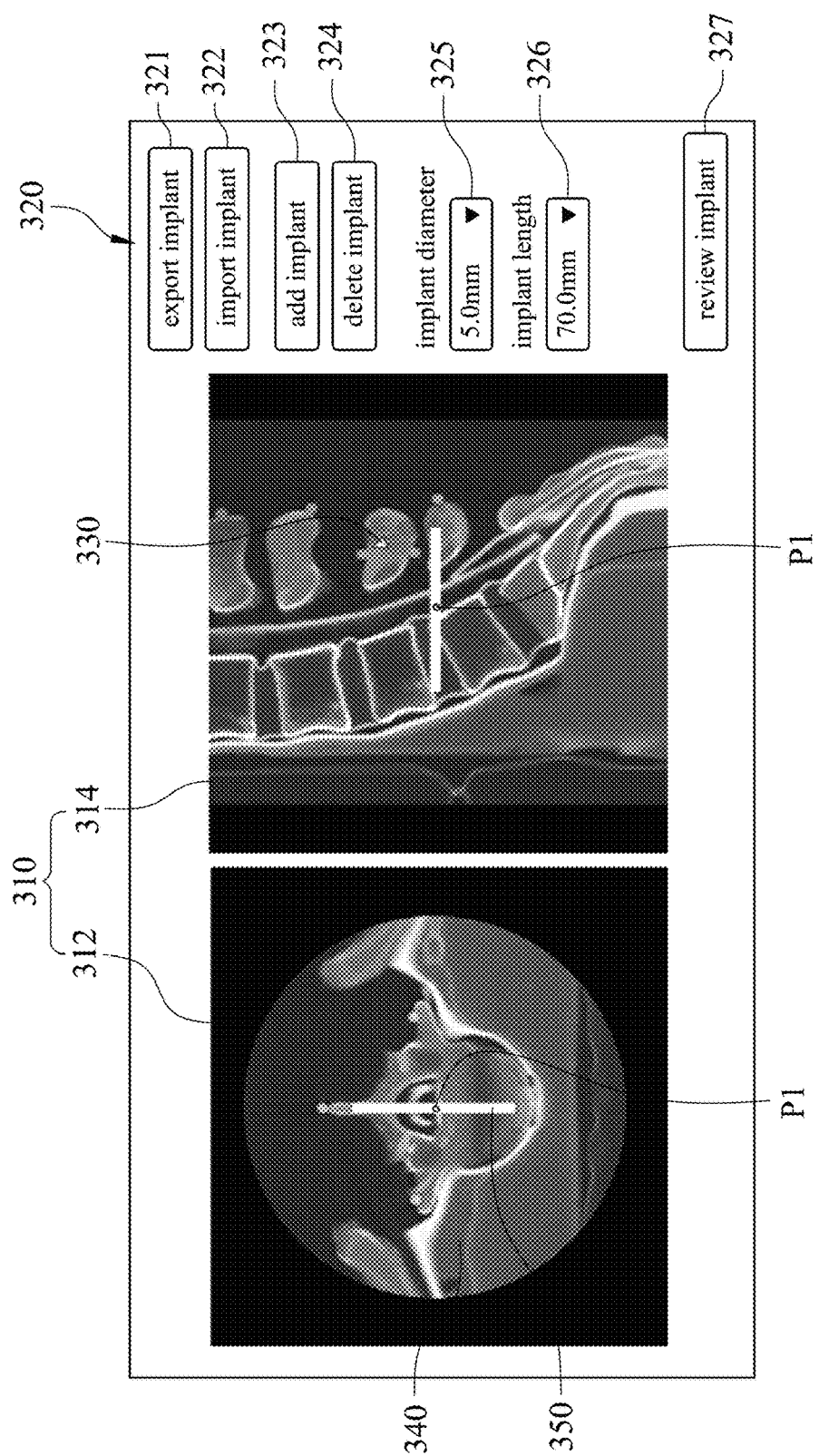
FIG. 3 shows a schematic view of an image of a screen according to a first embodiment of the present disclosure.
Figure 4:
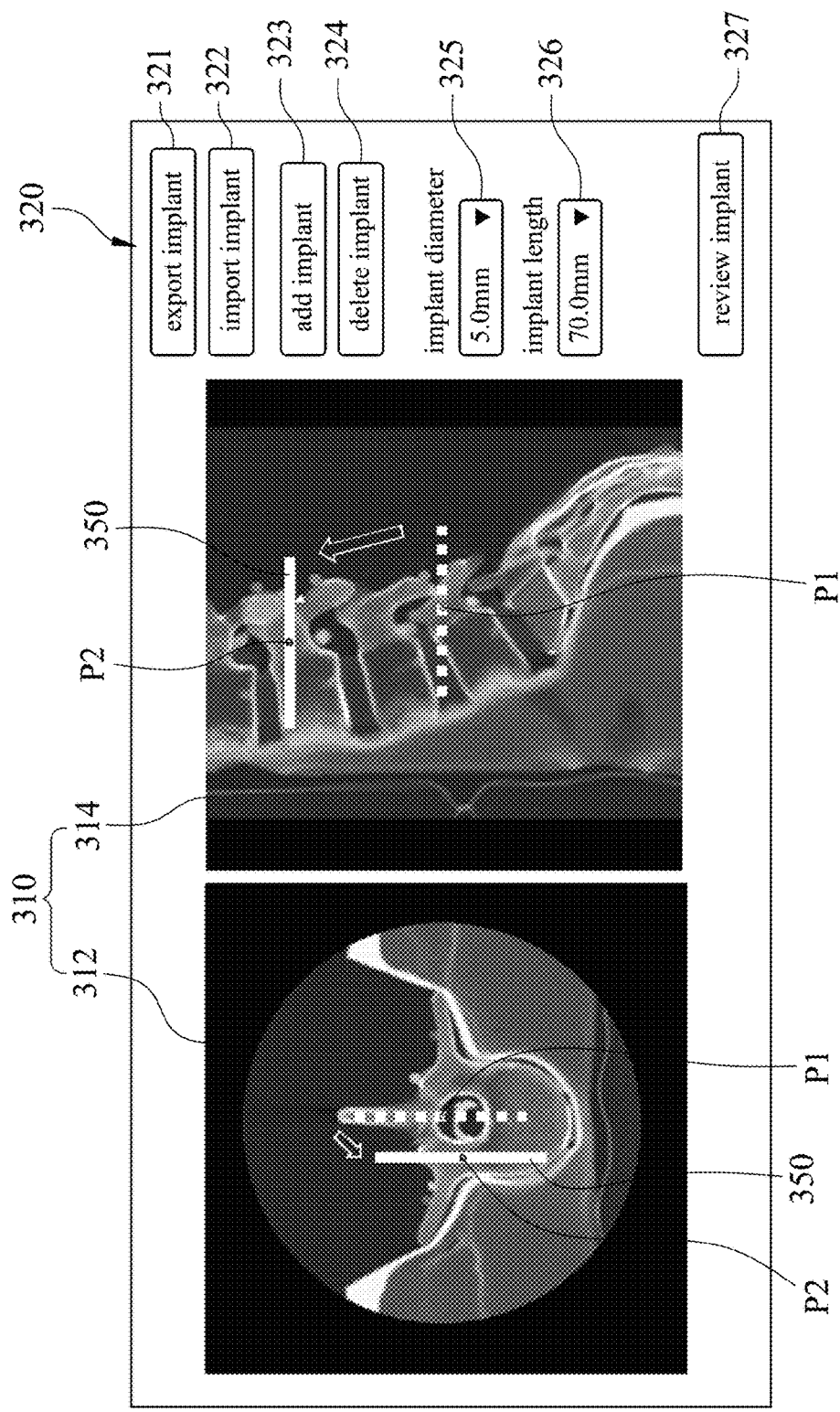
FIG. 4 shows a schematic view of an image of a screen according to a second embodiment of the present disclosure.
Figure 5:
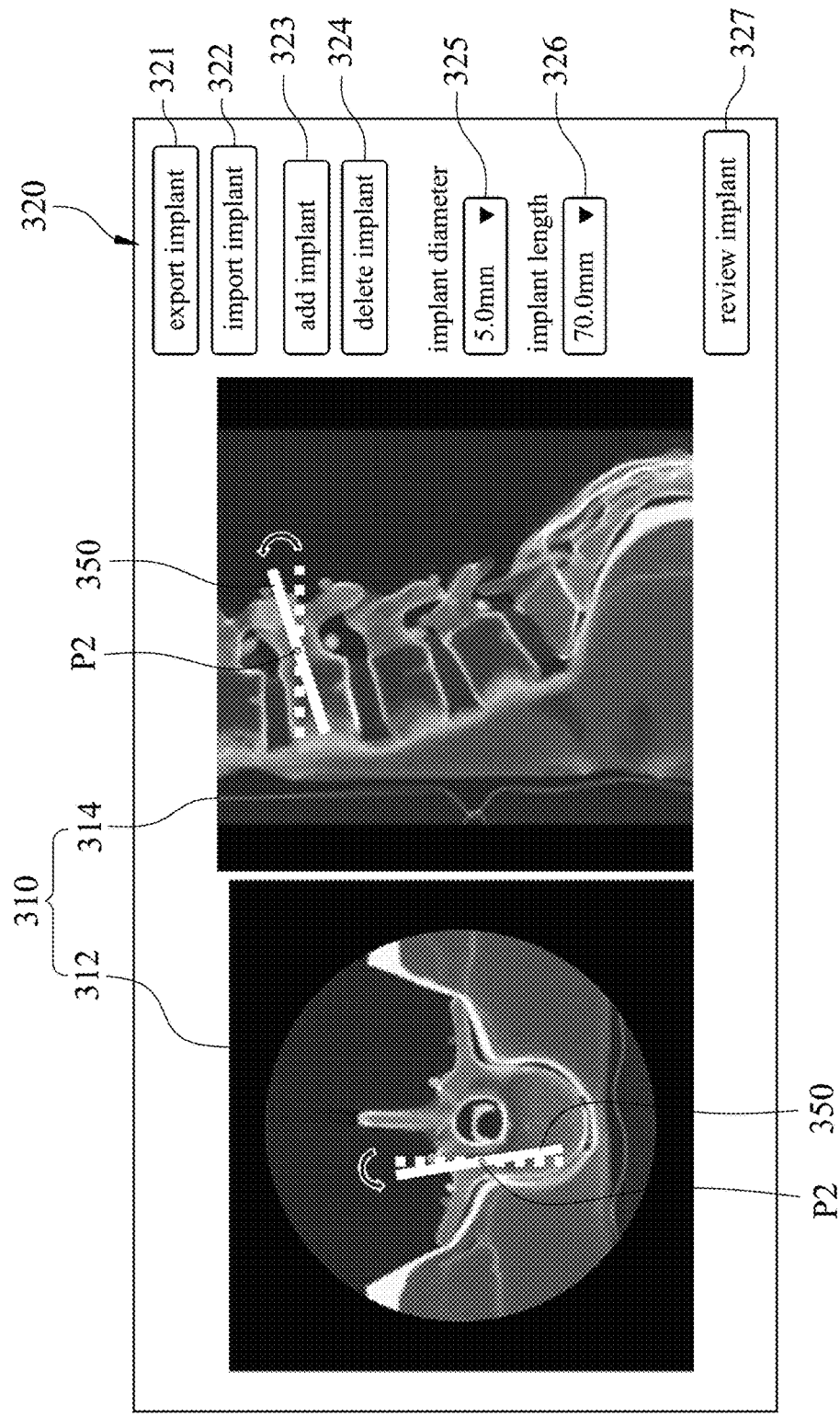
FIG. 5 shows a schematic view of an image of a screen according to a third embodiment of the present disclosure.
Figure 6A:
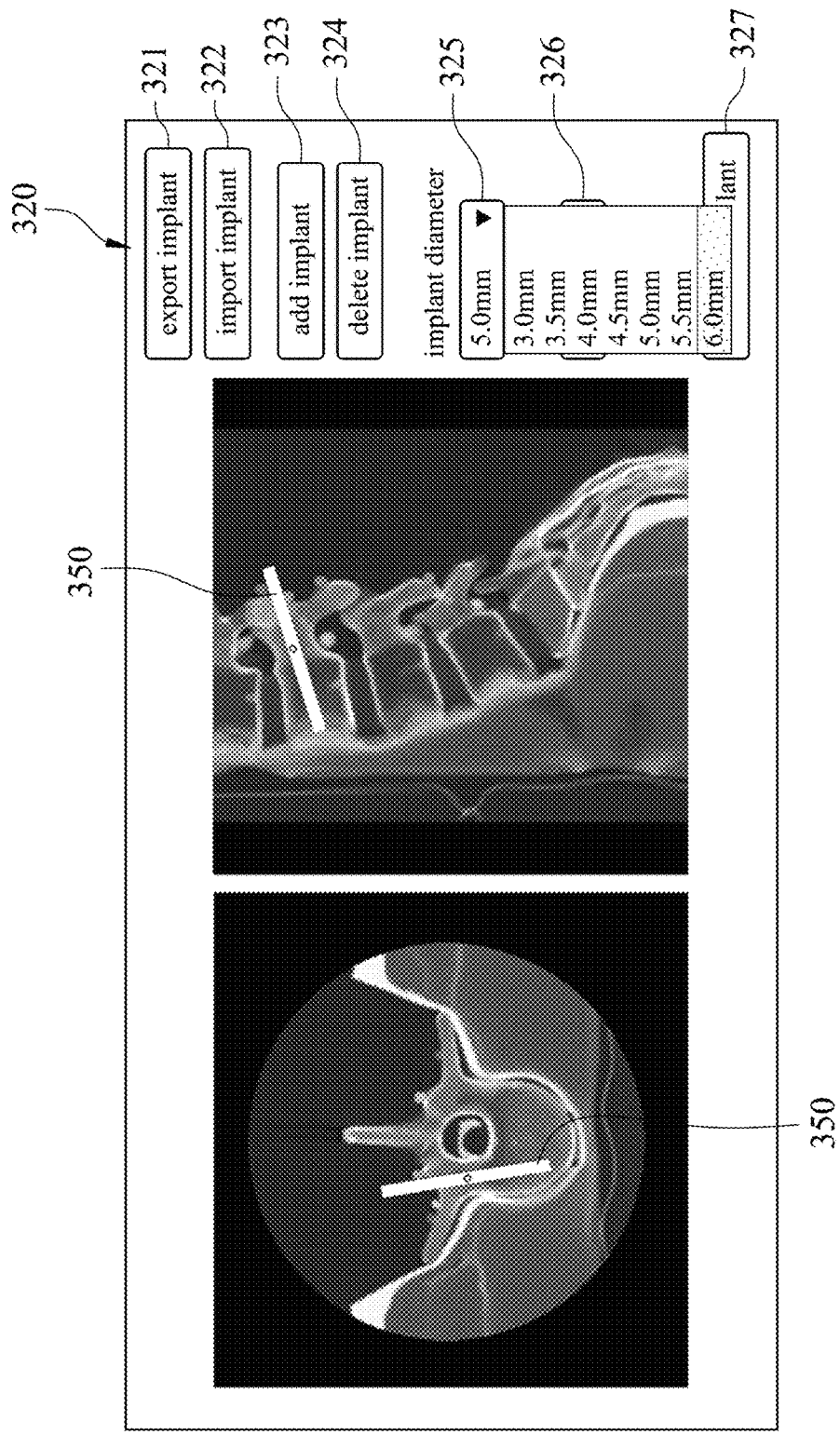
FIG. 6A shows a schematic view of an image of a screen according to a fourth embodiment of the present disclosure.
Figure 6B:
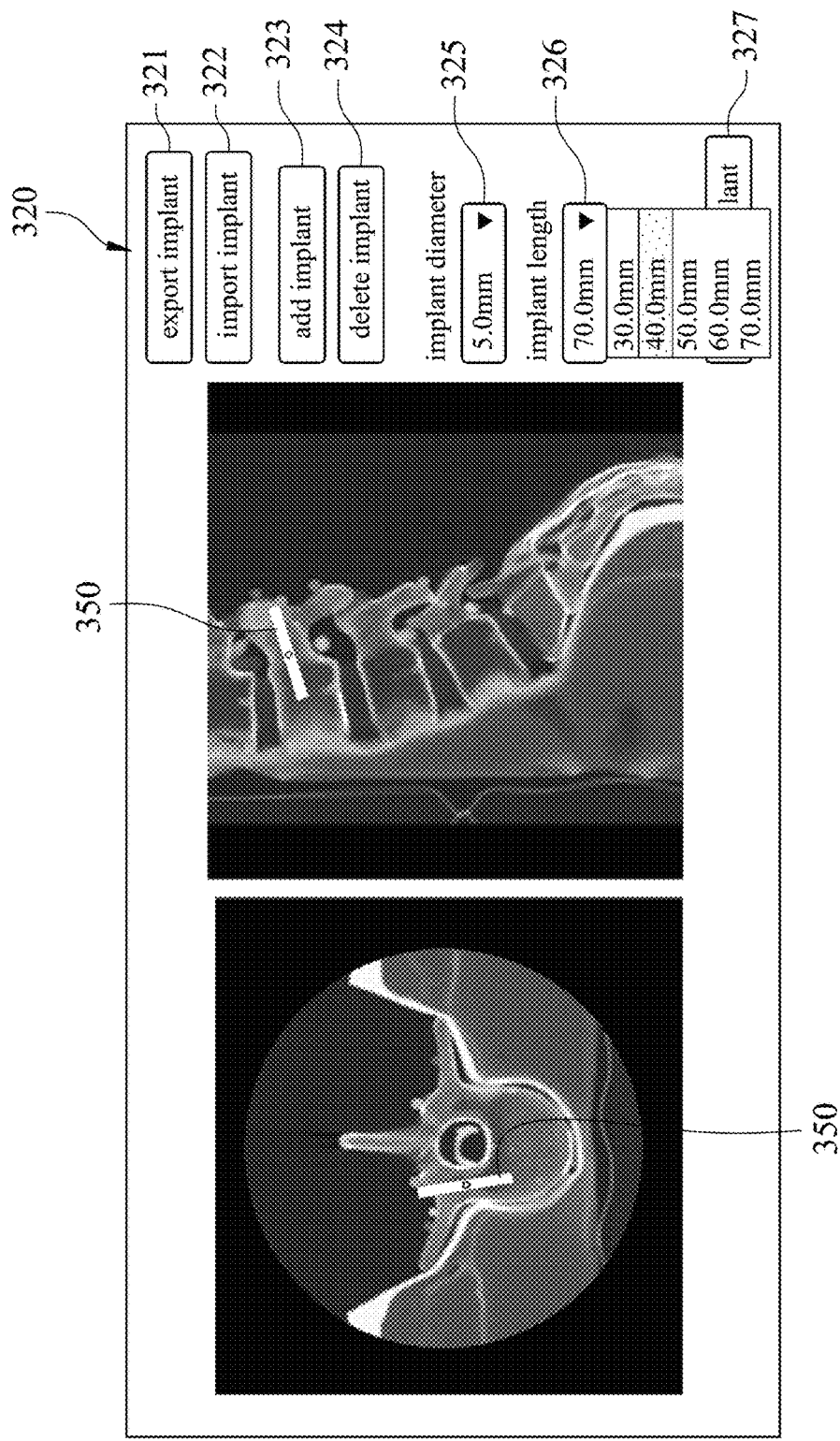
FIG. 6B shows a schematic view of an image of a screen according to a fifth embodiment of the present disclosure.
Figure 7:
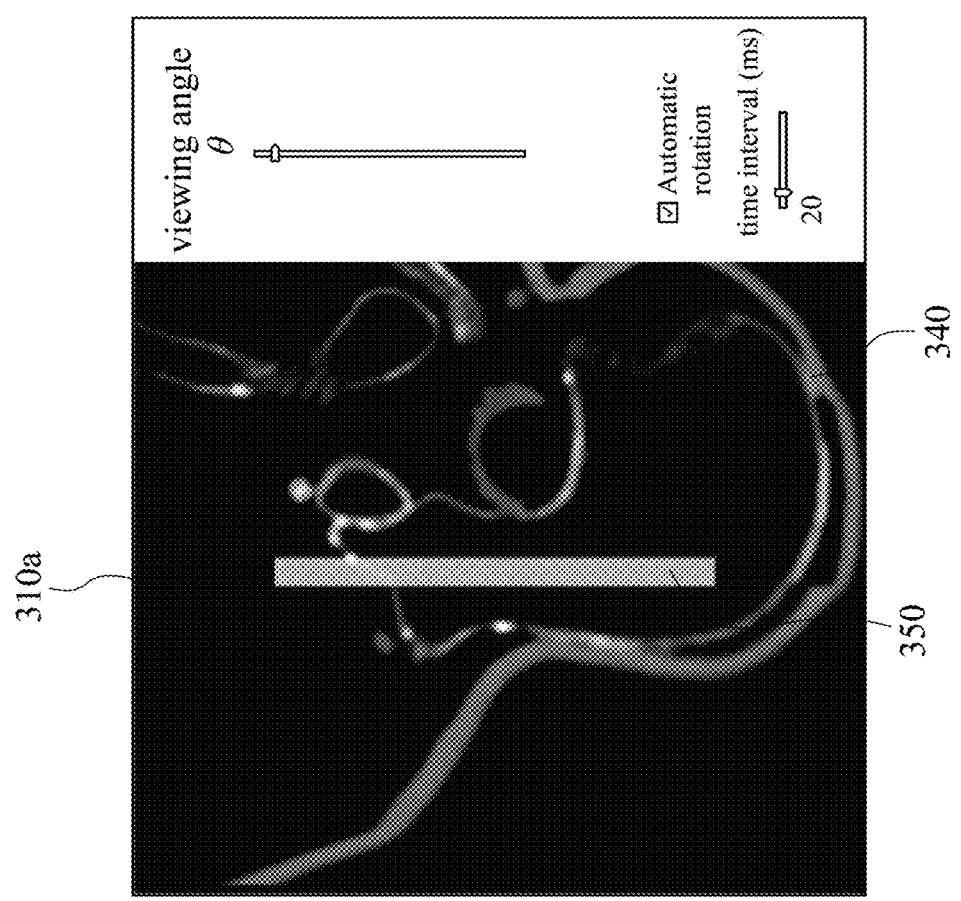
FIG. 7 shows a schematic view of an image of a screen according to a sixth embodiment of the present disclosure.

FIG. 1A shows a flow chart of a method 100 for verifying panoramic images of implants according to one embodiment of the present disclosure; FIG. 1B shows a block diagram of a system 200 for verifying panoramic images of implants according to one embodiment of the present disclosure; FIG. 3 shows a schematic view of an image of a screen 300 according to a first embodiment of the present disclosure; FIG. 4 shows a schematic view of an image of a screen according to a second embodiment of the present disclosure; FIG. 5 shows a schematic view of an image of a screen according to a third embodiment of the present disclosure; FIG. 6A shows a schematic view of an image of a screen according to a fourth embodiment of the present disclosure; FIG. 6B shows a schematic view of an image of a screen according to a fifth embodiment of the present disclosure; and FIG. 7 shows a schematic view of an image of a screen according to a sixth embodiment of the present disclosure. In addition, FIG. 3 shows a schematic view of an implant trajectory pattern 350 added in a picture 310 by a user, and the implant trajectory pattern 350 is located at a starting position P1. FIG. 4 represents that the implant trajectory pattern 350 is moved from the starting position P1 to a target position P2 in the picture 310 by the user. FIG. 5 represents that the implant trajectory pattern 350 is rotated by the user. FIG. 6A represents that one of implant diameters can be selected by the user. FIG. 6B represents that one of implant lengths can be selected by the user. FIG. 7 represents that panoramic images of an implant can be viewed by the user. A method 100 for verifying panoramic images of implants is used to check a relative position between the implant trajectory pattern 350 and a surgical site pattern 340. The method 100 can be combined with the system 200 for verifying panoramic images of implants. The implant trajectory pattern 350 and the surgical site pattern 340 are corresponding to the implant and a surgical site, respectively. The method 100 includes a pre-planning interface displaying step S11, an implant trajectory pattern adding step S12, an implant trajectory pattern adjusting step S13 and a panoramic image verifying step S14.

The pre-planning interface displaying step S11 is for displaying at least one picture 310, a menu 320 and a cursor 330 on a screen, and the picture 310 has the surgical site pattern 340, as shown in FIG. 3. The implant is a bone screw, and the implant trajectory pattern 350 is a bone screw image. The surgical site is a vertebral body, and the surgical site pattern 340 is a vertebral body image.

The implant trajectory pattern adding step S12 is for moving the cursor 330 to select an implant adding item of the menu 320 by the user and then generating the implant trajectory pattern 350 in the picture 310. The implant trajectory pattern 350 is located at a starting position P1, as shown in FIG. 3. In FIG. 3, the implant adding item of the menu 320 is corresponding to an add implant item 323. When the user controls the cursor 330 to click the add implant item 323, the implant trajectory pattern 350 is generated at a center of the picture 310, and the center of the picture 310 is set to the starting position P1. The three-dimensional coordinate (x, y, z) of the starting position P1 is (0, 0, 0).

The implant trajectory pattern adjusting step 313 is for controlling the cursor 330 to adjust a position of the implant trajectory pattern 350 and then move the implant trajectory pattern 350 from the starting position P1 to a target position P2 in the picture 310, as shown in FIGS. 4 and 5.

The panoramic image verifying step S14 is for rotating the surgical site pattern 340 around the implant trajectory pattern 350 at a viewing angle $\theta$ according to the target position P2 and the implant trajectory pattern 350 as a central axis, and the viewing angle $\theta$ is greater than 0 degrees and smaller than or equal to 180 degrees, as shown in FIG. 7. When the viewing angle $\theta$ is changed from 0 degrees to 180 degrees, only a first semicircular region surrounding the implant (0-180 degrees) is verified by the user. However, since the implant is a bone screw having a long cylindrical shape, a second semicircular region surrounding the implant (180-360 degrees) is reversely symmetrical to the first semicircular region surrounding the implant (0-180 degrees), so that the user, such as a physician, can conveniently verify whether or not the bone screw touches the vertebral body by the panoramic image verifying step S14 when the viewing angle $\theta$ is sequentially changed from 0 degrees to 180 degrees. Therefore, the panoramic image verifying step S14 of the present disclosure utilizes the 180-degree rotation of the surgical site pattern 340 around the implant trajectory pattern 350 as the central axis to allow physicians to correctly verify the relative positions of the bone screw and the vertebral body, thereby adaptively correcting the planning path and positions to improve the safety before surgical procedures.

In FIGS. 1B and 3-7, the system 200 for verifying panoramic images of implants and checking a relative position between the implant trajectory pattern 350 and the surgical site pattern 340 is a specific medical assist system cooperated with the method 100, and includes a screen 300 and a processing unit 400.

The screen 300 displays at least one picture 310, a menu 320 and a cursor 330, and the picture 310 has the surgical site pattern 340 and the implant trajectory pattern 350. The cursor 330 of the screen 300 can be controlled by a microphone, a keyboard, a mouse, a touch screen, a mobile device, a wireless communication device, or other similar input devices.

The processing unit 400 is signally connected to the screen 300. The processing unit 400 includes an implant trajectory pattern adding module 420, an implant trajectory pattern adjusting module 430 and a panoramic image verifying module 460. The implant trajectory pattern adding module 420 is configured to move the cursor 330 to select an implant adding item of the menu 320 by the user and then generate the implant trajectory pattern 350 in the picture. The implant trajectory pattern 350 is located at a starting position P1. The implant trajectory pattern adjusting module 430 is signally connected to the implant trajectory pattern adding module 420. The implant trajectory pattern adjusting module 430 is configured to control the cursor 330 to adjust a position of the implant trajectory pattern 350 and then move the implant trajectory pattern 350 from the starting position P1 to a target position P2 in the picture 310. The panoramic image verifying module 460 is signally connected to the implant trajectory pattern adjusting module 430. The panoramic image verifying module 460 is configured to rotate the surgical site pattern 340 around the implant trajectory pattern 350 at a viewing angle $\theta$ according to the target position P2 and the implant trajectory pattern 350 as a central axis, and the viewing angle $\theta$ is greater than 0 degrees and smaller than or equal to 180 degrees. When the viewing angle $\theta$ is sequentially changed from 0 degrees to 180 degrees, a first semicircular region surrounding the implant (0-180 degrees) can be verified by the user, and a second semicircular region surrounding the implant (180-360 degrees) is reversely symmetrical to the first semicircular region surrounding the implant (0-180 degrees). Certainly, the viewing angle $\theta$ may be greater than 180 degrees and smaller than or equal to 360 degrees according to the user's needs. In other words, the viewing angle $\theta$ can be sequentially changed from 0 degrees to 360 degrees in order to completely verify panoramic images of the implant. Accordingly, the system 200 of the present disclosure can use the 180-degree or 360-degree rotation of the surgical site pattern 340 around the implant trajectory pattern 350 as the central axis to allow physicians to correctly verify the relative positions of the bone screw and the vertebral body, thus conveniently verifying whether or not the bone screw touches the vertebral body.

Figure 2A:
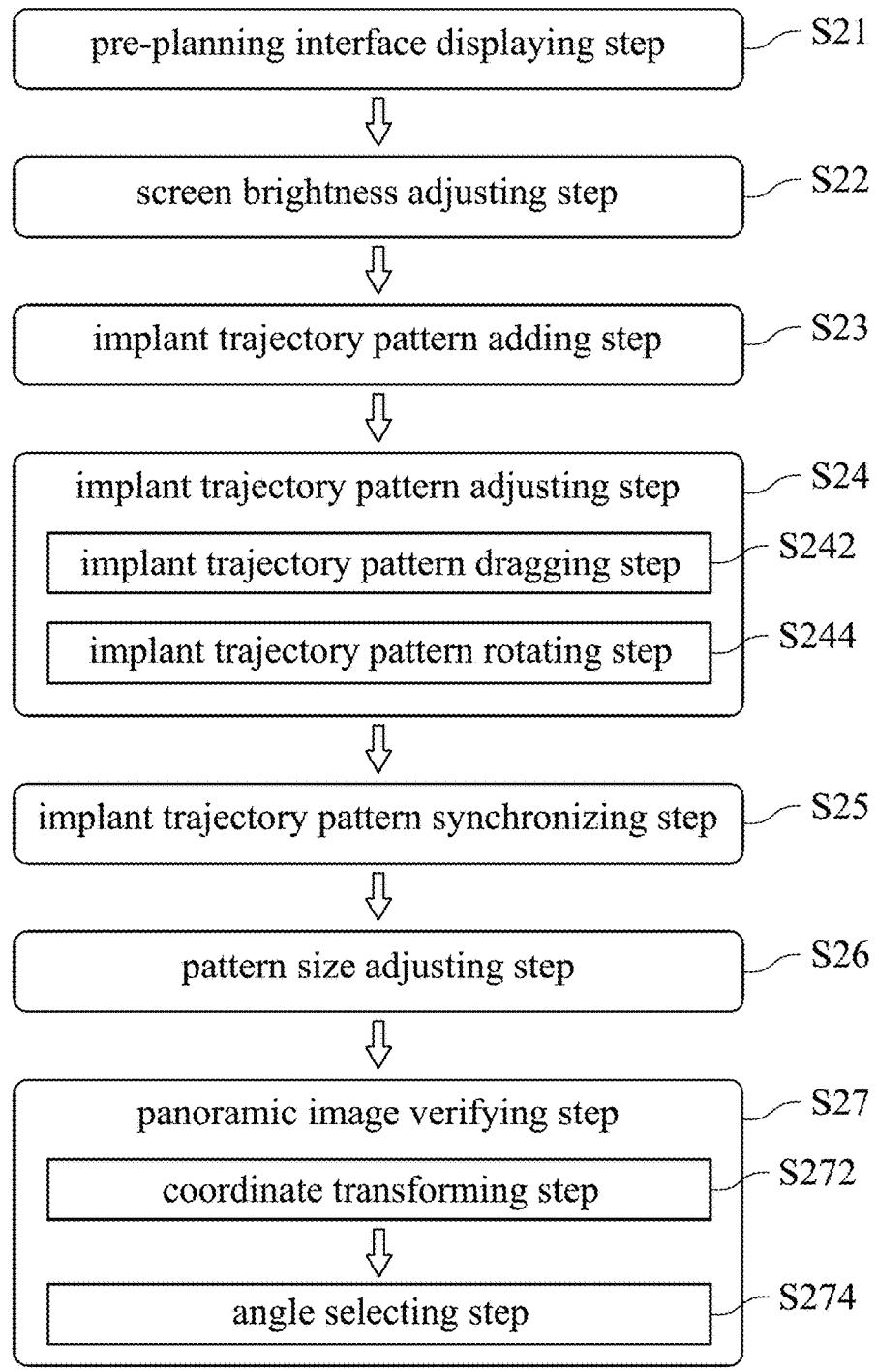
FIG. 2A shows a flow chart of a method for verifying panoramic images of implants according to another embodiment of the present disclosure.
Figure 2B:
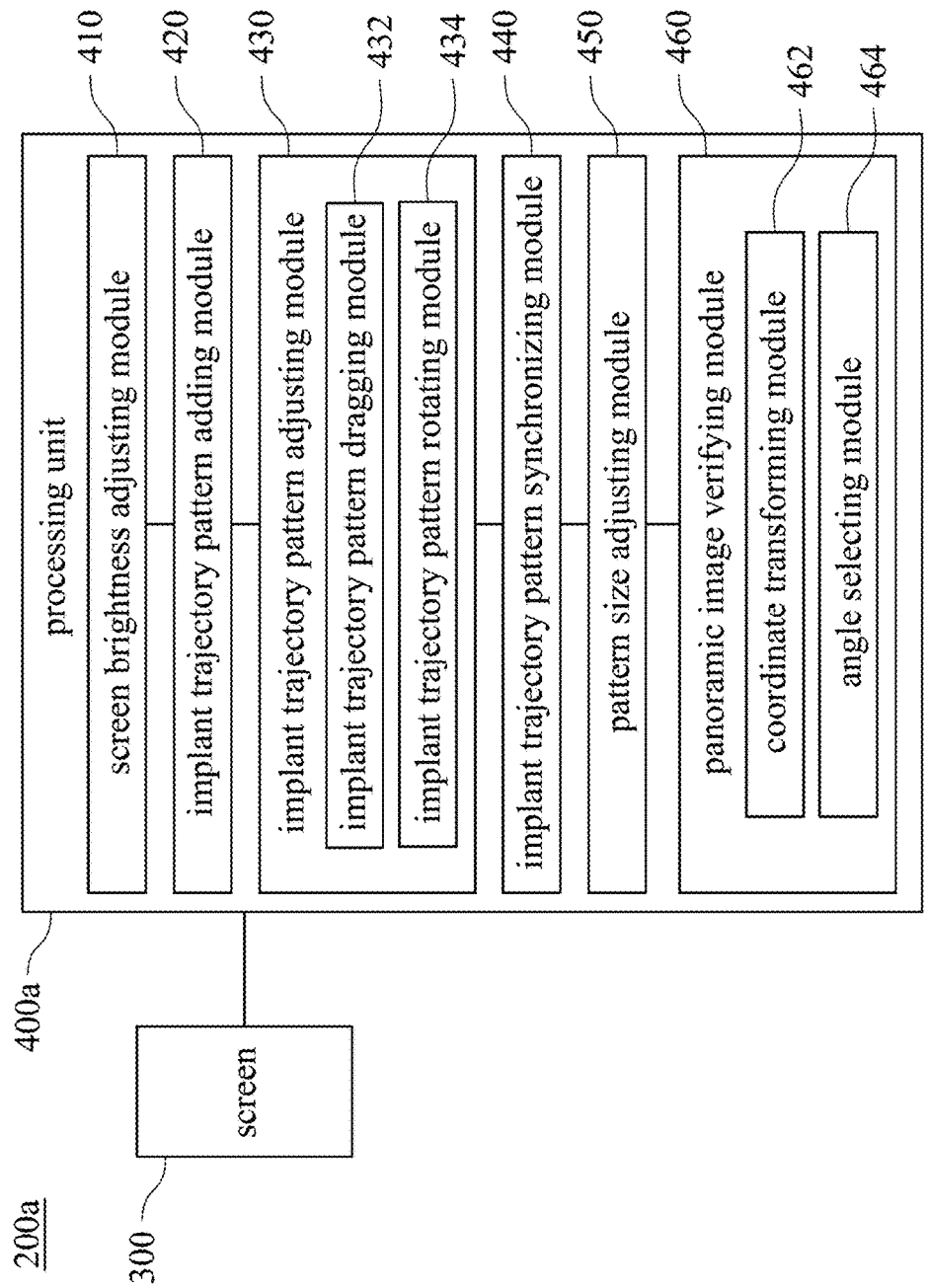
FIG. 2B shows a block diagram of a system for verifying panoramic images of implants according to another embodiment of the present disclosure.

FIG. 2A shows a flow chart of a method 100a for verifying panoramic images of implants according to another embodiment of the present disclosure; and FIG. 2B shows a block diagram of a system 200a for verifying panoramic images of implants according to another embodiment of the present disclosure. In FIGS. 2A, 2B and 3-7, the method 100a cooperated with the system 200a is used to check a relative position between an implant trajectory pattern 350 and a surgical site pattern 340. The method 100a includes a pre-planning interface displaying step S21, a screen brightness adjusting step S22, an implant trajectory pattern adding step S23, an implant trajectory pattern adjusting step S24, an implant trajectory pattern synchronizing step S25, a pattern size adjusting step S26 and a panoramic image verifying step S27.

The pre-planning interface displaying step S21 is for displaying two pictures 310, a menu 320 and a cursor 330 on a screen, and each of the pictures has the surgical site pattern 340. In detail, the two pictures 310 are a transverse plane 312 and a sagittal plane 314, respectively. The transverse plane 312 and the sagittal plane 314 are obtained by a computed tomography (CT) scanner or a magnetic resonance imaging (MRI) scanner. The transverse plane 312 is defined by an area between an x-axis and a z-axis. The sagittal plane 314 is defined by an area between the z-axis and a y-axis. The x-axis, the y-axis and the z-axis define a surgical site coordinate system. The three-dimensional coordinates of the implant (such as the bone screw) and the surgical site (such as the vertebral body) in the surgical site coordinate system can be shown in each of the pictures 310 to allow the user to review. In addition, the menu 320 includes an export implant item 321, an import implant item 322, an add implant item 323, a delete implant item 324, an implant diameter item 325, an implant length item 326 and a review implant item 327. The export implant item 321 represents the item of "export implant". After selecting the export implant item 321, a plurality of parameters of the bone screw (such as the implant diameter and the implant length) are transferred into an integrated file, and then the integrated file is stored in a hard disk or a database. The import implant item 322 represents the item of "import implant". After selecting the import implant item 322, the pre-stored integrated file can be read out from the hard disk or the database. The add implant item 323 represents the item of "add implant". After selecting the add implant item 323, a bone screw image is generated in each of the pictures 310, i.e., the implant trajectory pattern 350 is generated in each of the pictures 310. The delete implant item 324 represents the item of "delete implant". After selecting the delete implant item 324, one implant trajectory pattern 350 in each of the pictures 310 can be removed. The implant diameter item 325 and the implant length item 326 represent a diameter and a length of the implant (i.e., a bone screw diameter and a bone screw length), respectively. After selecting the implant diameter item 325 or the implant length item 326, a drop-down menu will appear, and the drop-down menu has different sizes to choose. The review implant item 327 represents the item of "review implant". After selecting the review implant item 327, the implant trajectory pattern 350, the surgical site pattern 340 and the viewing angle θ are displayed in another picture 310a on the screen. The surgical site pattern 340 is rotated around the implant trajectory pattern 350 as the central axis when the viewing angle H is sequentially changed from 0 degrees to 180 degrees. Moreover, the rotating mode can be chosen by the user from a manual rotation mode and an automatic rotation mode. The implant trajectory pattern 350, the surgical site pattern 340 and the viewing angle θ are displayed in the picture 310a according to a specific time interval and an angular interval. In FIG. 7, the time interval is 20 ms, and the angular interval is 1 degrees. Certainly, the user can freely set and modify the time interval and the angular interval.

The screen brightness adjusting step 322 is for moving the cursor 330 in the picture 310 via a mouse and activating a mouse button by the user to adjust brightness of the picture 310. In detail, the pictures 310 include the transverse plane 312 and the sagittal plane 314. When the cursor 330 (i.e., the mouse cursor) is located in the transverse plane 312, and the user presses the mouse button and moves the mouse, the brightness of the transverse plane 312 and the sagittal plane 314 is synchronously changed according to the moving condition of the mouse. Furthermore, a moving direction of the cursor 330 in the transverse plane 312 or the sagittal plane 314 can be adjusted to increase or decrease the brightness intensity. If the moving direction of the cursor 330 is from left to right or from bottom to top, the brightness intensity is increased. On the contrary, if the moving direction of the cursor 330 is from right to left or from top to bottom, the brightness intensity is decreased. Hence, the screen brightness adjusting step S22 of the present disclosure can quickly and efficiently adjust the brightness of the screen 310 by a simple operation.

The implant trajectory pattern adding step S23 is for moving the cursor 330 to select an implant adding item of the menu 320 by the user and then generating the implant trajectory pattern 350 in the picture 310. The implant trajectory pattern 350 is located at a starting position P1. In FIG. 3, the pictures 310 include the transverse plane 312 and the sagittal plane 314. After selecting the add implant item 323 by the cursor 330, two implant trajectory patterns 350 are generated in the centers of the transverse plane 312 and the sagittal plane 314, respectively. The centers of the transverse plane 312 and the sagittal plane 314 are both set to be the starting position P1, and the three-dimensional coordinate (x, y, z) of the starting position P1 is (0, 0, 0). In other words, the center position of each implant trajectory pattern 350 overlaps the starting position P1. In one embodiment, the surgical site is a vertebral body, and the surgical site pattern 340 is a vertebral body image. The implant is a bone screw, and the implant trajectory pattern 350 is a bone screw image. The bone screw image has an implant diameter and an implant length which are corresponding to the implant diameter item 325 and the implant length item 326 of the menu 320, respectively. The transverse plane 312 is parallel to an XY plane, and the sagittal plane 314 is parallel to a YZ plane. When the implant trajectory pattern 350 is moved in the transverse plane 312, the parameters x, y in the three-dimensional coordinate (x, y, z) of the center position of the implant trajectory pattern 350 are changed, and the parameter z is fixed and remains unchanged. Similarly, when the implant trajectory pattern 350 is moved in the sagittal plane 314, the parameters y, z in the three-dimensional coordinate (x, y, z) of the center position of the implant trajectory pattern 350 are changed, and the parameter x is fixed and remains unchanged. The three-dimensional coordinate (x, y, z) of the center position of the implant trajectory pattern 350 may be displayed in the pictures 310, i.e., the three-dimensional coordinate (x, y, z) of the center position of the implant trajectory pattern 350 may be simultaneously displayed in the transverse plane 312 and the sagittal plane 314, so that the user is able to correctly verify the relative positions of the implant trajectory pattern 350 and the surgical site pattern 340 in real time.

The implant trajectory pattern adjusting step S24 is for controlling the cursor 330 to adjust a position of the implant trajectory pattern 350 and then move the implant trajectory pattern 350 from the starting position P1 to a target position P2 in the picture 310. In the implant trajectory pattern adjusting step S24, the implant trajectory pattern 350 includes an intermediate point and a non-intermediate region. The cursor 330 is controlled to select the intermediate point or the non-intermediate region by the user. The implant trajectory pattern adjusting step S24 provides an implant trajectory pattern dragging step S242 and an implant trajectory pattern rotating step S244. When the cursor 330 is controlled to select the intermediate point, the implant trajectory pattern dragging step S242 is performed. The implant trajectory pattern dragging step S242 is for controlling the cursor 330 to point to the intermediate point by the mouse, and then dragging the intermediate point by activating the mouse button of the mouse so as to synchronously moving the implant trajectory pattern 350 and the cursor 330 in the picture 310, as shown in FIG. 4. No matter what the implant trajectory pattern 350 in the transverse plane 312 or in the sagittal plane 314 is selected, the implant trajectory pattern 350 can be dragged by the cursor 330. In other words, when the cursor 330 is located at the intermediate point, and the user presses the mouse button and moves the mouse, the implant trajectory pattern 350 is synchronously moved with the cursor 330 as a drag operation. Moreover, when the cursor 330 is controlled to select the non-intermediate region, the implant trajectory pattern rotating step S244 is performed. The implant trajectory pattern rotating step S244 is for controlling the cursor 330 to point to the non-intermediate region by the mouse, and then rotating the non-intermediate region by activating the mouse button so as to rotate the implant trajectory pattern 350 around the intermediate point, as shown in FIG. 5. The implant trajectory pattern dragging step S242 and the implant trajectory pattern rotating step S244 are not performed simultaneously. In the implant trajectory pattern rotating step S244, the implant trajectory pattern 350 in the picture is changed from a first color to a second color when the cursor 330 is pointed to the non-intermediate region by the user, and the first color is different from the second color. In one embodiment, the first color is cyan, and the second color is red. The different colors between the first color and the second color can allow the user to quickly recognize that the current operating mode is to rotate the implant image 350 by the cursor 330.

The implant trajectory pattern synchronizing step S25 and the implant trajectory pattern adjusting step S24 occur together. If there is only one picture 310 on the screen, the implant trajectory pattern synchronizing step S25 will not be performed. If there are two or more pictures 310 on the screen, such as the transverse plane 312 and the sagittal plane 314, the implant trajectory pattern synchronizing step S25 will be performed. The implant trajectory pattern synchronizing step S25 is for generating a transverse-plane implant trajectory pattern in the transverse plane 312, and generating a sagittal-plane implant trajectory pattern in the sagittal plane 314 after the implant trajectory pattern adding step S23. The transverse-plane implant trajectory pattern represents the implant trajectory pattern 350 in the transverse plane 312. The sagittal-plane implant trajectory pattern represents the implant trajectory pattern 350 in the sagittal plane 314. When the implant trajectory pattern adjusting step S24 is performed, and the transverse-plane implant trajectory pattern is moved by the cursor 330 in the transverse plane 312, the sagittal-plane implant trajectory pattern is simultaneously moved in the sagittal plane 314 according to the surgical site coordinate system, and the surgical site pattern 340 corresponding to the sagittal-plane implant trajectory pattern is simultaneously changed in the sagittal plane 314. On the other hand, when the implant trajectory pattern adjusting step S24 is performed, and the sagittal-plane implant trajectory pattern is moved by the cursor 330 in the sagittal plane 314, the transverse-plane implant trajectory pattern is simultaneously moved in the transverse plane 312 according to the surgical site coordinate system, and the surgical site pattern 340 corresponding to the transverse-plane implant trajectory pattern is simultaneously changed in the transverse plane 312. Therefore, the present disclosure uses the implant trajectory pattern synchronizing step S25 combined with the implant trajectory pattern adjusting step S24 to allow the user to quickly and correctly drag the implant image 350 to the target position P2 in the transverse plane 312 and the sagittal plane 314, so that the implant image 350 is rotated to an appropriate tilt angle for observation and verifying.

The pattern size adjusting step S26 is for controlling the cursor 330 to select an implant size item of the menu 320 by the user. The implant size item includes a plurality of implant diameters and a plurality of implant lengths. When one of the implant diameters and one of the implant lengths are selected by the cursor 330, a diameter and a length of the implant trajectory pattern 350 displayed in the picture 310 are correspondingly changed according to the selected implant diameter and the selected implant length, respectively. In detail, the implant size item includes the implant diameter item 325 and the implant length item 326. The implant diameter item 325 and the implant length item 326 represent the diameter and the length of the implant (i.e., the bone screw diameter and the bone screw length), respectively. After selecting the implant diameter item 325 or the implant length item 326, a drop-down menu will appear, and the drop-down menu has different sizes to choose by the user. In one embodiment, the drop-down menu of the implant diameter item 325 has 3.0 mm, 3.5 mm, 4.0 mm, 4.5 mm, 5.0 mm, 5.5 mm and 6.0 mm, as shown in FIG. 6A. The drop-down menu of the implant length item 326 has 30.0 mm, 40.0 mm, 50.0 mm, 60.0 mm and 70.0 mm, as shown in FIG. 6B. Certainly, the user can freely set and modify the sizes of the diameter and the length, the diameter intervals and the length intervals. Accordingly, the pattern size adjusting step S26 of the present disclosure provides a flexible selection to satisfy the needs of patient and surgery. Moreover, the sizes of the diameter and the length can be transferred into the integrated file, and then the integrated file is stored in the hard disk or the database after selecting the export implant item 321 of the menu 320. The integrated file can be imported directly in the future if necessary so as to greatly improve the efficiency of preoperative planning.

The panoramic image verifying step S27 is for controlling the cursor 330 to select a panoramic image verifying item 327 of the menu 320 by the user, and then rotating the surgical site pattern 340 around the implant trajectory pattern 350 at a viewing angle θ according to the target position P2 and the implant trajectory pattern 350 as a central axis. The viewing angle θ is greater than 0 degrees and smaller than or equal to 180 degrees. In detail, the panoramic image verifying step S27 includes a coordinate transforming step S272 and an angle selecting step S274. After selecting the panoramic image verifying item 327, the coordinate transforming step S272 is first performed, and then the angle selecting step S274 is performed. The coordinate transforming step S272 is for establishing an implant coordinate system according to the target position P2 and the implant trajectory pattern 350 as the central axis, and then converting coordinates of the surgical site pattern 340 from the surgical site coordinate system into a reconstructed surgical site coordinate system according to the implant coordinate system. The angle selecting step S274 is for selecting the viewing angle θ and rotating the surgical site pattern 340 of the reconstructed surgical site coordinate system around the central axis at the viewing angle θ. When the viewing angle θ is sequentially changed from 0 degrees to 180 degrees, the physician can conveniently verify whether or not the bone screw touches the vertebral body. In addition, the screen can display a plurality of pictures, such as the pictures 310, 310a. The panoramic image verifying step S27 is for displaying the implant trajectory pattern 350, the surgical site pattern 340 and the viewing angle θ in the picture 310a on the screen, thereby enabling users to view the relationship between the implant trajectory pattern 350 and the surgical site pattern 340, as shown in FIG. 7. The suitable rotating mode can be chosen by the user from the automatic rotation mode and the manual rotation mode. The automatic rotation mode represents that the picture 310a automatically displays the implant trajectory pattern 350 and the surgical site pattern 340 at the viewing angle θ during the time interval (about 20 ms). The angular interval of the viewing angle θ is 1 degrees. The manual rotation mod represents that the user manually controls the mouse and the cursor 330 to choose the viewing angle θ. Hence, the panoramic image verifying step S27 of the present disclosure employs the 180-degree or 360-degree rotation of the surgical site pattern 340 around the implant trajectory pattern 350 as the central axis to allow physicians to correctly verify the relative positions of the bone screw and the vertebral body, thereby adaptively correcting the planning path and positions to improve the safety before surgical procedures.

In FIG. 2B, the system for verifying panoramic images of implants includes a screen 300 and a processing unit 400a. The processing unit 400a includes a screen brightness adjusting module 410, an implant trajectory pattern adding module 420, an implant trajectory pattern adjusting module 430, an implant trajectory pattern synchronizing module 440, a pattern size adjusting module 450 and a panoramic image verifying module 460. The details of the screen 300 and the implant trajectory pattern adding module 420 of the processing unit 400a are the same as the screen 300 and the implant trajectory pattern adding module 420 of FIG. 1B, respectively. In FIG. 2B, the processing unit 400a further includes the screen brightness adjusting module 410, the implant trajectory pattern synchronizing module 440 and the pattern size adjusting module 450. The implant trajectory pattern adjusting module 430 includes an implant trajectory pattern dragging module 432 and an implant trajectory pattern rotating module 434. The panoramic image verifying module 460 includes a coordinate transforming module 462 and an angle selecting module 464.

The screen brightness adjusting module 410 is signally connected to the implant trajectory pattern adding module 420 and the screen 300. The screen 300 displays two pictures 310 which are a transverse plane 312 and a sagittal plane 314, respectively. The screen brightness adjusting module 410 is configured to move the cursor 330 in the one of the two pictures 310 via a mouse and activate a mouse button by the user to adjust brightness of the two pictures 310. The transverse plane 312 is defined by an area between an x-axis and a z-axis. The sagittal plane 314 is defined by an area between the z-axis and a y-axis. The x-axis, the y-axis and the z-axis define a surgical site coordinate system.

The implant trajectory pattern adding module 420 is configured to move the cursor 330 to select an implant adding item of the menu 320 by the user and then generate a transverse-plane implant trajectory pattern and a sagittal-plane implant trajectory pattern in the transverse plane 312 and the sagittal plane 314, respectively.

The implant trajectory pattern adjusting module 430 is signally connected to the implant trajectory pattern adding module 420. The implant trajectory pattern dragging module 432 is configured to control the cursor 330 to point to the intermediate point by a mouse and then drag the intermediate point by activating a mouse button of the mouse so as to synchronously moving the implant trajectory pattern 350 and the cursor 330 in the picture 310. Furthermore, the implant trajectory pattern rotating module 434 is configured to control the cursor 330 to point to the non-intermediate region by the mouse and then rotate the non-intermediate region by activating the mouse button so as to rotate the implant trajectory pattern 350 around the intermediate point.

The implant trajectory pattern synchronizing module 440 is signally connected to the implant trajectory pattern adjusting module 430. The implant trajectory pattern synchronizing module 440 is configured to detect the positions of the transverse-plane implant trajectory pattern and the sagittal-plane implant trajectory pattern in real time. When the transverse-plane implant trajectory pattern is moved in the transverse plane, the sagittal-plane implant trajectory pattern is simultaneously moved in the sagittal plane 314 according to the surgical site coordinate system, and the surgical site pattern 340 corresponding to the sagittal-plane implant trajectory pattern is simultaneously changed in the sagittal plane 314. On the other hand, when the sagittal-plane implant trajectory pattern is moved in the sagittal plane 314, the transverse-plane implant trajectory pattern is simultaneously moved in the transverse plane 312 according to the surgical site coordinate system, and the surgical site pattern 340 corresponding to the transverse-plane implant trajectory pattern is simultaneously changed in the transverse plane 312.

The pattern size adjusting module 450 is signally connected to the implant trajectory pattern synchronizing module 440 and the panoramic image verifying module 460. The pattern size adjusting module 450 is configured to control the cursor 330 to select an implant size item of the menu 320 by the user. The implant size item includes a plurality of implant diameters and a plurality of implant lengths. When one of the implant diameters and one of the implant lengths are selected by the cursor 330, a diameter and a length of the transverse-plane implant trajectory pattern displayed in the transverse plane 312 are correspondingly changed according to the selected implant diameter and the selected implant length. In addition, a diameter and a length of the sagittal-plane implant trajectory pattern displayed in the sagittal plane 314 are correspondingly changed according to the selected implant diameter and the selected implant length.

The panoramic image verifying module 460 is configured to rotate the surgical site pattern 340 around the implant trajectory pattern 350 at a viewing angle θ according to the target position P2 and the implant trajectory pattern 350 as a central axis. The panoramic image verifying module 460 includes a coordinate transforming module 462 and an angle selecting module 464. The coordinate transforming module 462 is signally connected to the pattern size adjusting module 450. The coordinate transforming module 462 is configured to establish an implant coordinate system according to the target position P2 and the implant trajectory pattern 350 as the central axis and then convert coordinates of the surgical site pattern 340 from the surgical site coordinate system into a reconstructed surgical site coordinate system according to the implant coordinate system. Moreover, the angle selecting module 464 is signally connected to the coordinate transforming module 462. The angle selecting module 464 is configured to select the viewing angle θ and rotating the surgical site pattern 340 of the reconstructed surgical site coordinate system around the central axis (i.e., the implant trajectory pattern 350) at the viewing angle θ. The viewing angle θ is greater than 0 degrees and smaller than or equal to 180 degrees. More preferably, the viewing angle θ is changed from 0 degrees to 180 degrees with the angular interval being 1 degrees. It represents that a semicircular region surrounding the implant trajectory pattern 350 (0-180 degrees) is verified by the user. Most preferably, the viewing angle θ is changed from 0 degrees to 360 degrees with the angular interval being 1 degrees. It represents that a whole region surrounding the implant trajectory pattern 350 (0-360 degrees) is completely verified by the user. The semicircular region of the vertebral body image surrounding the implant trajectory pattern 350 (180-360 degrees) is reversely symmetrical to the semicircular region of the vertebral body surrounding the implant (0-180 degrees), so that the physician can conveniently verify whether or not the bone screw touches the vertebral body and confirm the relative position between the bone screw and the vertebral body by the panoramic image verifying step S27 when the viewing angle θ is sequentially changed from 0 degrees to 180 degrees. If the relative position is incorrect or the vertebral body is too close to the bone screw, a location of the bone screw can be adaptively adjusted to correct the planning path and positions to improve the safety before surgical procedures.

According to the aforementioned embodiments and examples, the advantages of the present disclosure are described as follows.

1. The method and the system of the present disclosure use the 180-degree or 360-degree rotation of the surgical site pattern around the implant trajectory pattern as the central axis to allow physicians to correctly verify the relative positions of the bone screw and the vertebral body, thereby adaptively correcting the planning path and positions to improve the safety before surgical procedures.

2. The rotating mode can be chosen by the user from a manual rotation mode and an automatic rotation mode. The user can freely set and modify the time interval and the angular interval.

3. The different colors of the implant trajectory pattern can allow the user to quickly recognize that the current operating mode is to rotate the implant image by the cursor.

4. The present disclosure uses the implant trajectory pattern synchronizing step combined with the implant trajectory pattern adjusting step to allow the user to quickly and correctly drag the implant image to the target position in the transverse plane and the sagittal plane, so that the implant image is rotated to an appropriate tilt angle for observation and verifying.

5. The pattern size adjusting step of the present disclosure provides a flexible selection to satisfy the needs of patient and surgery.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A method for verifying panoramic images of implants and checking a relative position between an implant trajectory pattern and a surgical site pattern, the method comprising:
   providing a pre-planning interface displaying step, wherein the pre-planning interface displaying step is for displaying at least one picture, a menu and a cursor on a screen, and the picture has the surgical site pattern;
   providing an implant trajectory pattern adding step, wherein the implant trajectory pattern adding step is for moving the cursor to select an implant adding item of the menu by a user and then generating the implant trajectory pattern in the picture, and the implant trajectory pattern is located at a starting position;
   providing an implant trajectory pattern adjusting step, wherein the implant trajectory pattern adjusting step is for controlling the cursor to adjust a position of the implant trajectory pattern and then move the implant trajectory pattern from the starting position to a target position in the picture; and
   providing a panoramic image verifying step, wherein the panoramic image verifying step is for rotating the surgical site pattern around the implant trajectory pattern at a viewing angle according to the target position and the implant trajectory pattern as a central axis, and the viewing angle is greater than 0 degrees and smaller than or equal to 180 degrees;
   wherein the viewing angle θ is sequentially changed from 0 degrees to 180 degrees according to a time interval and an angular interval.

2. The method of claim 1, wherein the implant trajectory pattern is a bone screw image, the surgical site pattern is a vertebral body image, and the viewing angle is greater than 0 degrees and smaller than or equal to 360 degrees.

3. The method of claim 1, further comprising:
   providing a screen brightness adjusting step, wherein the screen brightness adjusting step is for moving the cursor in the picture via a mouse and activating a mouse button by the user to adjust brightness of the picture.

4. The method of claim 1, wherein,
   the pre-planning interface displaying step is for displaying a plurality of pictures on the screen, and the pictures comprises:
   a transverse plane defined by an area between an x-axis and a z-axis; and
   a sagittal plane defined by an area between the z-axis and a y-axis, wherein the x-axis, the y-axis and the z-axis define a surgical site coordinate system; and
   the implant trajectory pattern adding step is for moving the cursor to select the implant adding item of the menu by the user and then generate a transverse-plane implant trajectory pattern and a sagittal-plane implant trajectory pattern in the transverse plane and the sagittal plane, respectively.

5. The method of claim 4, further comprising:
providing an implant trajectory pattern synchronizing step, wherein the implant trajectory pattern synchronizing step is for detect positions of the transverse-plane implant trajectory pattern and the sagittal-plane implant trajectory pattern in real time;
wherein when the transverse-plane implant trajectory pattern is moved in the transverse plane, the sagittal-plane implant trajectory pattern is simultaneously moved in the sagittal plane according to the surgical site coordinate system;
wherein when the sagittal-plane implant trajectory pattern is moved in the sagittal plane, the transverse-plane implant trajectory pattern is simultaneously moved in the transverse plane according to the surgical site coordinate system.

6. The method of claim 1, wherein,
in the implant trajectory pattern adjusting step, the implant trajectory pattern comprises an intermediate point and a non-intermediate region, the cursor is controlled to select the intermediate point or the non-intermediate region by the user; and
the implant trajectory pattern adjusting step comprises:
providing an implant trajectory pattern dragging step, wherein the implant trajectory pattern dragging step is for controlling the cursor to point to the intermediate point by a mouse, and then dragging the intermediate point by activating a mouse button of the mouse so as to synchronously moving the implant trajectory pattern and the cursor in the picture; and
providing an implant trajectory pattern rotating step, wherein the implant trajectory pattern rotating step is for controlling the cursor to point to the non-intermediate region by the mouse, and then rotating the non-intermediate region by activating the mouse button so as to rotate the implant trajectory pattern around the intermediate point.

7. The method of claim 6, wherein,
in the implant trajectory pattern rotating step, the implant trajectory pattern in the picture is changed from a first color to a second color when the cursor is pointed to the non-intermediate region by the user, and the first color is different from the second color.

8. The method of claim 1, further comprising:
providing a pattern size adjusting step, wherein the pattern size adjusting step is for controlling the cursor to select an implant size item of the menu by the user, the implant size item comprises a plurality of implant diameters and a plurality of implant lengths, and when one of the implant diameters and one of the implant lengths are selected by the cursor, a diameter and a length of the implant trajectory pattern displayed in the picture are correspondingly changed according to the selected implant diameter and the selected implant length, respectively.

9. The method of claim 1, wherein the panoramic image verifying step comprises:
providing a coordinate transforming step, wherein the coordinate transforming step is for establishing an implant coordinate system according to the target position and the implant trajectory pattern as the central axis, and then converting coordinates of the surgical site pattern from a surgical site coordinate system into a reconstructed surgical site coordinate system according to the implant coordinate system; and
providing an angle selecting step, wherein the angle selecting step is for selecting the viewing angle and rotating the surgical site pattern of the reconstructed surgical site coordinate system around the central axis at the viewing angle.

10. The method of claim 1, wherein,
the pre-planning interface displaying step is for displaying a plurality of pictures on the screen, and two of the pictures are a transverse plane and a sagittal plane, respectively; and
the panoramic image verifying step is for displaying the implant trajectory pattern, the surgical site pattern and the viewing angle in another picture on the screen.

11. A system for verifying panoramic images of implants and checking a relative position between an implant trajectory pattern and a surgical site pattern, the system comprising:
a screen displaying at least one picture, a menu and a cursor, and the picture having the surgical site pattern; and
a processing unit signally connected to the screen, and comprising:
an implant trajectory pattern adding module configured to move the cursor to select an implant adding item of the menu by a user and then generate the implant trajectory pattern in the picture, wherein the implant trajectory pattern is located at a starting position;
an implant trajectory pattern adjusting module signally connected to the implant trajectory pattern adding module, wherein the implant trajectory pattern adjusting module is configured to control the cursor to adjust a position of the implant trajectory pattern and then move the implant trajectory pattern from the starting position to a target position in the picture; and
a panoramic image verifying module signally connected to the implant trajectory pattern adjusting module, wherein the panoramic image verifying module is configured to rotate the surgical site pattern around the implant trajectory pattern at a viewing angle according to the target position and the implant trajectory pattern as a central axis, and the viewing angle is greater than 0 degrees and smaller than or equal to 180 degrees;
wherein the viewing angle $\theta$ is sequentially changed from 0 degrees to 180 degrees according to a time interval and an angular interval.

12. The system of claim 11, wherein the implant trajectory pattern is a bone screw image, the surgical site pattern is a vertebral body image, and the viewing angle is greater than 0 degrees and smaller than or equal to 360 degrees.

13. The system of claim 11, wherein the processing unit further comprises:
a screen brightness adjusting module signally connected to the implant trajectory pattern adding module and the screen, wherein the screen brightness adjusting module is configured to move the cursor in the picture via a mouse and activate a mouse button by the user to adjust brightness of the picture.

14. The system of claim 11, wherein the screen displays a plurality of pictures, and the pictures comprises:
a transverse plane defined by an area between an x-axis and a z-axis; and
a sagittal plane defined by an area between the z-axis and a y-axis, wherein the x-axis, the y-axis and the z-axis define a surgical site coordinate system.

15. The system of claim 14, wherein, the implant trajectory pattern adding module is configured to move the cursor to select the implant adding item of the menu by the user and then generate a transverse-plane implant trajectory pattern and a sagittal-plane implant trajectory pattern in the transverse plane and the sagittal plane, respectively; and the processing unit further comprises an implant trajectory pattern synchronizing module signally connected to the implant trajectory pattern adjusting module, wherein the implant trajectory pattern synchronizing module is configured to detect positions of the transverse-plane implant trajectory pattern and the sagittal-plane implant trajectory pattern in real time;

wherein when the transverse-plane implant trajectory pattern is moved in the transverse plane, the sagittal-plane implant trajectory pattern is simultaneously moved in the sagittal plane according to the surgical site coordinate system by the implant trajectory pattern synchronizing module;

wherein when the sagittal-plane implant trajectory pattern is moved in the sagittal plane, the transverse-plane implant trajectory pattern is simultaneously moved in the transverse plane according to the surgical site coordinate system by the implant trajectory pattern synchronizing module.

16. The system of claim 11, wherein the implant trajectory pattern comprises an intermediate point and a non-intermediate region, the cursor is controlled by the user to select the intermediate point or the non-intermediate region, and the implant trajectory pattern adjusting module comprises:

an implant trajectory pattern dragging module configured to control the cursor to point to the intermediate point by a mouse and then drag the intermediate point by activating a mouse button of the mouse so as to synchronously moving the implant trajectory pattern and the cursor in the picture; and an implant trajectory pattern rotating module configured to control the cursor to point to the non-intermediate region by the mouse and then rotate the non-intermediate region by activating the mouse button so as to rotate the implant trajectory pattern around the intermediate point.

17. The system of claim 16, wherein the implant trajectory pattern in the picture is changed from a first color to a second color when the cursor is pointed to the non-intermediate region by the user, and the first color is different from the second color.

18. The system of claim 11, wherein the processing unit further comprises:

a pattern size adjusting module signally connected to the panoramic image verifying module, wherein the pattern size adjusting module is configured to control the cursor to select an implant size item of the menu by the user, the implant size item comprises a plurality of implant diameters and a plurality of implant lengths, and when one of the implant diameters and one of the implant lengths are selected by the cursor, a diameter and a length of the implant trajectory pattern displayed in the picture are correspondingly changed according to the selected implant diameters and the selected implant lengths.

19. The system of claim 11, wherein the panoramic image verifying module comprises:

a coordinate transforming module configured to establish an implant coordinate system according to the target position and the implant trajectory pattern as the central axis and then convert coordinates of the surgical site pattern from a surgical site coordinate system into a reconstructed surgical site coordinate system according to the implant coordinate system; and an angle selecting module signally connected to the coordinate transforming module, wherein the angle selecting module is configured to select the viewing angle and rotating the surgical site pattern of the reconstructed surgical site coordinate system around the central axis at the viewing angle.

20. The system of claim 11, wherein, the screen displays a plurality of pictures, and two of the pictures are a transverse plane and a sagittal plane, respectively; and the panoramic image verifying module is configured to display the implant trajectory pattern, the surgical site pattern and the viewing angle in another picture on the screen.

\* \* \* \* \*